(12) United States Patent
Christensen (10) Patent No.: US 7,985,208 B2
(45) Date of Patent: Jul. 26, 2011

(54) RING SHAPED CONTOURED COLLAGEN SHIELD FOR OPHTHALMIC DRUG DELIVERY

(75) Inventor: James M. Christensen, Glendora, CA (US)

(73) Assignee: Oasis Research LLC, Glendora, CA (US)

( * ) Notice: Subject to any disclaimer, the term of this patent is extended or adjusted under 35 U.S.C. 154(b) by 488 days.

(21) Appl. No.: 12/233,510

(22) Filed: Sep. 18, 2008

(65) Prior Publication Data

US 2010/0069857 A1    Mar. 18, 2010

(51) Int. Cl.
*A61M 35/00* (2006.01)
*G02C 7/04* (2006.01)
(52) U.S. Cl. .................. 604/294; 424/428; 424/429
(58) Field of Classification Search .......... 604/294, 604/300; 424/428, 429
See application file for complete search history.

(56) References Cited

U.S. PATENT DOCUMENTS

| | | | | |
|---|---|---|---|---|
| 3,485,244 A * | 12/1969 | Rosen | ............... | 424/429 |
| 3,618,604 A * | 11/1971 | Ness | ............... | 604/294 |
| 3,786,812 A | 1/1974 | Neefe | | |
| 3,867,519 A * | 2/1975 | Michaels | ............... | 424/473 |
| 3,960,150 A * | 6/1976 | Hussain et al. | ............... | 424/428 |
| 4,186,184 A * | 1/1980 | Zaffaroni | ............... | 424/427 |
| 4,201,210 A * | 5/1980 | Hughes et al. | ............... | 424/428 |
| 4,484,922 A | 11/1984 | Rosenwald | | |
| 4,540,417 A * | 9/1985 | Poler | ............... | 424/429 |
| 4,592,752 A | 6/1986 | Neefe | | |
| 4,820,038 A * | 4/1989 | Seger et al. | ............... | 351/160 H |
| 5,067,961 A * | 11/1991 | Kelman et al. | ............... | 623/5.16 |
| 5,270,051 A | 12/1993 | Harris | | |
| 5,378,475 A * | 1/1995 | Smith et al. | ............... | 424/473 |
| 5,431,790 A * | 7/1995 | Nesburn et al. | ............... | 204/157.68 |
| 5,472,436 A | 12/1995 | Fremstad | | |
| 5,824,086 A * | 10/1998 | Silvestrini | ............... | 623/5.11 |
| 6,096,076 A * | 8/2000 | Silvestrini | ............... | 623/5.12 |
| 6,132,735 A | 10/2000 | Harris et al. | | |
| 7,303,278 B2 * | 12/2007 | Perel et al. | ............... | 351/177 |
| 2004/0073303 A1 * | 4/2004 | Schanzlin et al. | ............... | 623/5.16 |
| 2006/0024350 A1 | 2/2006 | Varner et al. | | |
| 2006/0257451 A1 | 11/2006 | Varner et al. | | |
| 2006/0290882 A1 * | 12/2006 | Meyers et al. | ............... | 351/160 H |
| 2007/0016292 A1 * | 1/2007 | Perez | ............... | 623/5.13 |
| 2007/0071792 A1 | 3/2007 | Varner et al. | | |
| 2008/0243095 A1 * | 10/2008 | Kaiser et al. | ............... | 604/294 |
| 2008/0317819 A1 * | 12/2008 | Orilla et al. | ............... | 424/429 |
| 2009/0004244 A1 * | 1/2009 | Orilla et al. | ............... | 424/429 |

* cited by examiner

*Primary Examiner* — Jacqueline F Stephens
*Assistant Examiner* — Paula L Craig
(74) *Attorney, Agent, or Firm* — Koppel, Patrick, Heybl & Philpott; Michael J. Ram (57) ABSTRACT

A collagen corneal shield for placement on the outer surface of the eye for protection of the eye, for delivery of drugs to the eye, or for both protection and drug delivery to the eye, functions without obstructing vision. The shield has a first, central portion comprising non-crosslinked collagen capable of rapid decomposition in the presence of enzymes in the tears, and a second portion comprising crosslinked collagen which decomposes slowly in the presence of enzymes in the tears so that it remains on the eye for a period of time longer than the first portion. The first portion of the shield covers the central portion of the cornea and the second portion of the shield extends outward from the first portion. As a result of decomposition of the first portion the corneal shield becomes a ring or washer shape around the central portion and at least a portion of the cornea is no longer covered by the shield so that vision is not obstructed. The corneal shield can also be contoured so that it has one or more base curve radii selected to provide retention of the shield on the eye.

5 Claims, 7 Drawing Sheets fig.1 fig.2

RING SHAPED CONTOURED COLLAGEN SHIELD FOR OPHTHALMIC DRUG DELIVERY

The present invention relates to a vehicle for protection of the eye or delivery of therapeutic drugs or other medications or beneficial compounds to the eye utilizing a contoured shield placed on the exterior of the cornea and sclera, the shield being sized and processed so that when in use the central portion of the shield decomposes thereby creating a washer-shaped shield which does not interfere with the vision of the user.

BACKGROUND

Figure 1:
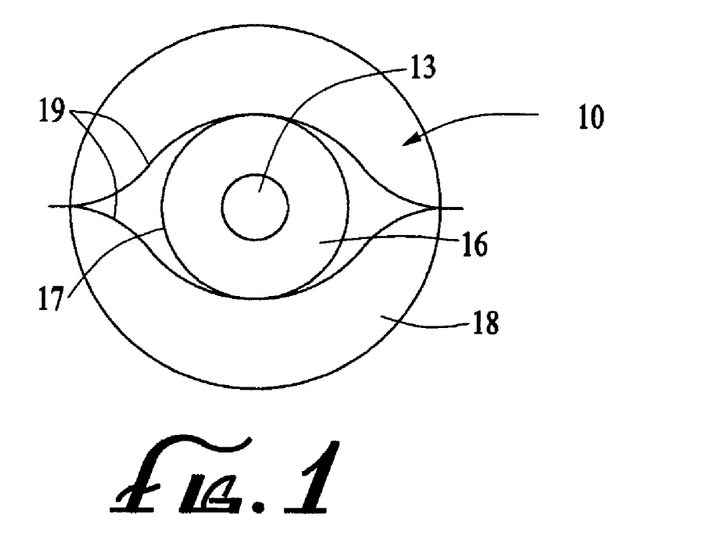
FIG. 1 is a front view schematic representation of the eye.
Figure 2:
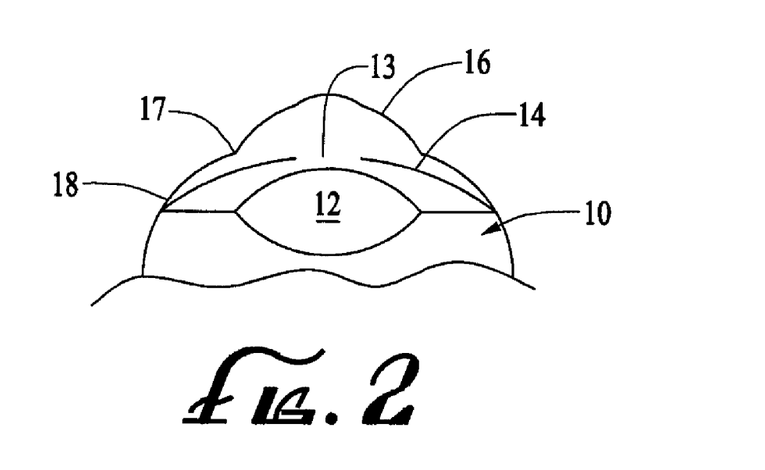
FIG. 2 is a schematic representation of the front portion of the eye taken in cross section.

FIGS. 1 and 2 are schematic representations of the eye 10. Referring to FIGS. 1 and 2, the inner portion 12 is the lens which is located behind the iris 14 and is visible through the central open portion of the iris 13. The front central outer portion of the eye comprises a transparent tissue, referred to as the cornea 16, which, as seen in side view (see FIG. 2) has a radius smaller than the radius of the eye and appears to bulge from the eye. The typical radius of the cornea is 7.7 mm while the eyeball itself has a radius of about 13.5 mm. The white portion of the eyeball surrounding the cornea is referred to as the sclera 18 and the junction of the cornea with the sclera is referred to as the limbus 17. The eyelids 19 are moveable over the cornea and acts to cover and protect the eye.

Collagen corneal shields, which are provided as generally hemispheric contact lenses, have been available since the 1990s. One purpose of these devices, following placement on the eye, is to protect the eye during healing. Another purpose of these devices is the delivery of drugs to the surface of the eye following cataract surgery and other ophthalmic procedures. The drugs have been primarily antibiotics to prevent infection and steroids to reduce inflammation. The collagen shields are supplied as dehydrated films which are soaked in aqueous solutions of drugs in concentrations suitable for topical delivery just prior to their placement on the eye.

Once the hydrated collagen shield is placed on the eye, it begins to break down or decompose due to contact with the enzymes in the tears on the surface of the eye. The amount of crosslinking induced in the collagen shield by UV irradiation during manufacture determines the length of time the shield will remain intact and on the eye. In general, upon contact with enzymes that are present in the tears on the eye, the shield will begin to swell and become cloudy, resulting in a loss of transparency. The inner base curve of the shield will begin to increase in diameter and the shield will become unstable and be pushed around on the eye by the eyelids. Eventually the shield will either come off the eye in the case of a long-lasting shield (several days), or decompose on the eye in the case of a short-term (one day) shield.

The loss of transparency of the collagen shields shortly after being placed on the eye is the biggest problem with the collagen shields. Because the whole shield, including the central corneal portion becomes cloudy, the patient's vision through the shield is decreased so that the wearer has only a perception of light and dark and the patient is not able to perform normal activities such as driving or reading. This presents a hazard to the patient in that the patient looses the use of the eye during the period the shield is on the eye. There is a need for a collagen shield that does not decrease the patient's vision, but provides the benefits of protecting the eye or dosing a drug to the eye from a matrix, that matrix eventually being removed from the eye, comes off the eye, or decomposes on the eye.

Several patents and publications show and describe alternative ring or washer shaped devices which do not obstruct the central vision of the cornea. However, the biggest problem with these washer-shaped devices is the ability to place them on the eye. Since they are thin and flexible, these devices curl up easily and are difficult to unfold onto the eye. Further, when placed on the eye, they tend to stretch out of shape, do not fit on the eye as intended, and do not stabilize on the eye. As a result, these washer-shaped devices are easily moved around on the eye by the motion of the eyelid over the device.

Rosenwald, U.S. Pat. No. 4,484,922, describes an annular shaped drug delivery washer with walls that have a slight spherical curvature to generally match the curvature of the eye. The Rosenwald ring shaped device is designed to be placed outward from the limbus so that it is only on the scleral portion of the eye. The diameter of the central open portion of the ring or washer is approximately 11-12 mm and the width of the drug delivery portion is 2-4 mm resulting in an outer edge diameter of 16-20 mm. The thickness of the washer is 0.1-0.2 mm. The washer is supposed to be held in place on the eye by the eyelids in the conjunctival area of the eye. However, the large central opening of the washer does not provide enough body to support the fragile collagen washer from being distorted by the movement of the eyelid over the device.

The Fremstad patent, U.S. Pat. No. 5,472,436, is similar to the Rosenwald patent in that it is also a scleral drug delivery washer or ring and is similar in size to the Rosenwald washer. The Fremstad washer is also designed to be placed outward from the limbus on the scleral portion of the eye. It is flat in shape, i.e., no spherical curvature, and has a thickness of 0.05-0.1 mm. Since it is flat, slits are placed in the flat washer to allow it to conform to the curvature of the scleral region of the eye when it is placed on the eye. This collagen washer-shaped device is even more prone than the Rosenwald washer to being pushed around the eye by the eyelids since it is thinner and more fragile, and lacks an inner curvature to stabilize it on the eye.

U.S. Pat. No. 4,592,752 to Neefe describes a drug delivery washer having smaller diameter openings and is designed to fit over the cornea. The outer edge of the washer may remain on the cornea or extend just past the cornea onto the scleral portion of the eye. The washer has an inner opening with an edge diameter of 4-7 mm, allowing vision through a small central portion of the washer. The outer edge of the washer may vary from 10-16 mm diameter which may result in the outer edge extending past the limbus. The inner edge of the washer (i.e., around the central opening) is tapered to prevent a tear meniscus from forming at this inner edge and distorting vision, and to minimize the foreign body sensation when the eyelid rubs across the washer. The Neefe device has a single concave base curve (the portion contacting the eye surface) with a radius of curvature varying from 5.43-9.85 mm to allow for the corneal curvature under different vision conditions (from 48-39 diopters). The surface of the ring has a contour different from the contacting surface contour, with a steep convex curve at the periphery in order to provide a thin outer edge. It also has a flat convex curve in the central portion of the outer surface of washer in order to create an opening in the central portion of the washer while providing a thin edge in this area. Further, the Neefe washer is designed to flex and adapt to the eye. This feature, along with the single base curve, enables the washer to be easily pushed around on the eye since the base curve of the washer cannot match both the curvature of the cornea and scleral region of the eye.

U.S. Pat. No. 5,270,051 to Harris is one of a series of patents which describe the use of the enzyme hyaluronidase to soften the cornea in an orthokeratology procedure. In this procedure, a rigid lens or washer is used to alter the shape of the cornea after the hyaluronidase has been applied to the cornea. One embodiment is a washer shaped rigid lens for use in hyperopic eyes. The central opening of the lens allows a space for the cornea to deform into during the orthokeratology procedure. The Harris lens is designed to fit over the cornea of the eye. The outer diameter of the lens is 6.85-10.5 mm, and the diameter of the hole in the center of the hyperopic lens varies between 2.5-4.5 mm. The base curve of the hyperopic lens is comprised of three curves with the radius varying from 5.5-9.5 mm. These curves are selected to shape the cornea to its final contour and to retain the lens on the cornea. This is a rigid lens which is not designed to protect the eye or to dose drugs to the eye. It is intended to deform the eye in order to reform the eye to a different contour.

Each of the prior non-rigid washer or ring-shaped devices is designed to fit either on the cornea or on the sclera and therefore have only a single base curve to match the corneal radius or the scleral radius respectively. They do not avail themselves of the stability to be gained having multiple radii which would enable the washer to lock into the limbus of the eye where the corneal contour transitions into the scleral contour.

Thus, there is still a need for an improved collagen shield for protection of the eye or delivery of drugs to the surface of the eye following cataract surgery and other ophthalmic procedures, or both, that does not obstruct the patient's vision and remains stable on the eye.

SUMMARY OF THE INVENTION

The present disclosure provides a generally hemispheric contoured shield formed from collagen, or a similar performing material, only a portion of which is crosslinked to provide a desired retention time of the shield on the eye. The shield is placed on the eye covering the cornea and a portion of the sclera for protection of the eye, or delivery of a drug to the eye, or both, over an extended period of time. The central corneal portion of the shield is not crosslinked so that it will rapidly decompose once placed on the eye, leaving a washer or ring-shaped shield which does not obstruct central corneal vision. The shield can be formed with a single radius base curve, with a dual-radii base curve wherein the two radii form a limbal ring on the shield consistent with the limbus of the eye when the shield is placed on the eye, or with multiple radii which comprise its base curve. The outer edge of the shield may be circular or irregular in shape, as desired, to increase coverage on the eye or to provide a more stable retention of the shield on the eye. The central opening which results in the shield shortly after it is placed on the eye, has a diameter sufficient to not obstruct the visual path of the eye during normal variations of the opening of the iris.

DETAILED DISCUSSION

A crosslinked collagen shield design for placement on the eye to protect the eye and/or for the delivery of drugs to the eye, and a method of its manufacture, is disclosed. The shield in its packaged configuration is shaped to cover both the cornea and sclera. However, soon after application to the eye the central portion of the shield covering at least a portion of the cornea decomposes leaving that portion of the cornea unshielded. The collagen shield can be supplied either prehydrated or can be supplied as a dehydrated film which could be hydrated just prior to placement of the shield on the eye. Hydration is provided by use of aqueous solutions, such as solutions of drugs, such as antibiotics to prevent infection or steroids to reduce inflammation, in concentrations which are suitable for topical delivery. The shield can be easily removed from its packaging and handled and will retain its shape when placed on the eye without curling, stretching, or distorting. It covers the cornea and extends beyond the cornea onto the scleral portion of the eye to provide additional protection or drug delivery to the surface. Preferably, the shield has a compound base curve which matches the curvature of the cornea and scleral portions of the eye thereby enabling the shield to fixate in the limbal region of the eye. After the shield has been placed on the eye, the central corneal portion of the shield will enzymatically decompose leaving a washer-shaped shield which will remain stable on the eye for extended periods of time without being repositioned by normal movements of the eye and without obstructing the patient's visual pathway.

Figure 3:
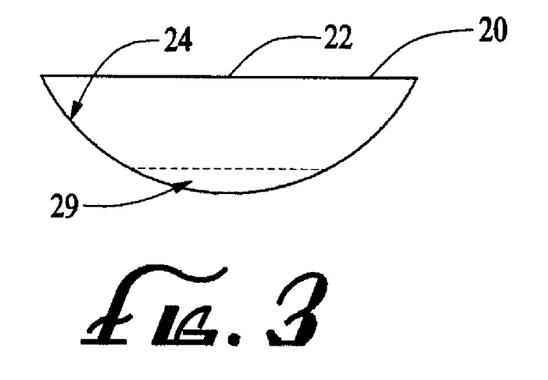
FIG. 3 is a side view of a first embodiment showing a shield incorporating features of the invention with a single-radius base curve.
Figure 4:
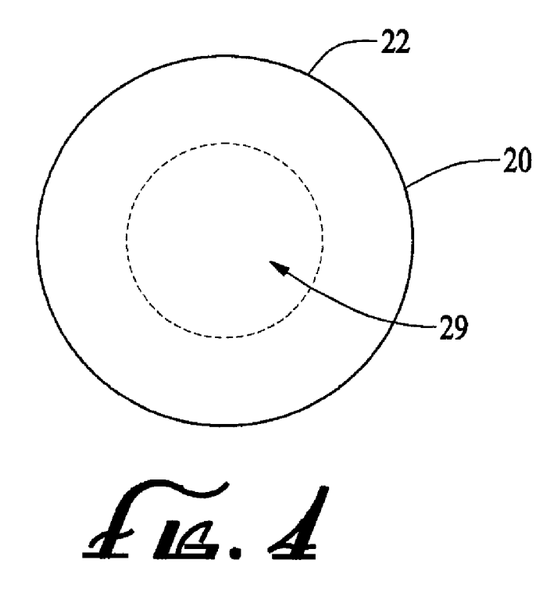
FIG. 4 is a front view of the shield of FIG. 3.

Referring to FIGS. 3 and 4, a first embodiment of the device described herein is shown. The collagen shield 20 has a single-radius base curve 24 sized to fit on the eye and cover the cornea and a portion of the scleral region of the eye. The radius of curvature of the base curve is approximately 10 mm, which is larger than the typical corneal radius of curvature of 7.7 mm and smaller than the typical scleral radius of curvature of 13.5 mm. The outer edge 22 of the collagen shield has a circular configuration with an outer diameter of approximately 17-18 mm. When placed on the eye, this collagen shield will loosely fit over the cornea and limbal regions of the eye and stabilize where the outer edge 22 of the shield contacts the scleral portion of the eye. The central corneal portion 29 of the shield, which decomposes shortly after the shield is placed on the eye, has a diameter of approximately 8-9 mm.

Figure 5:
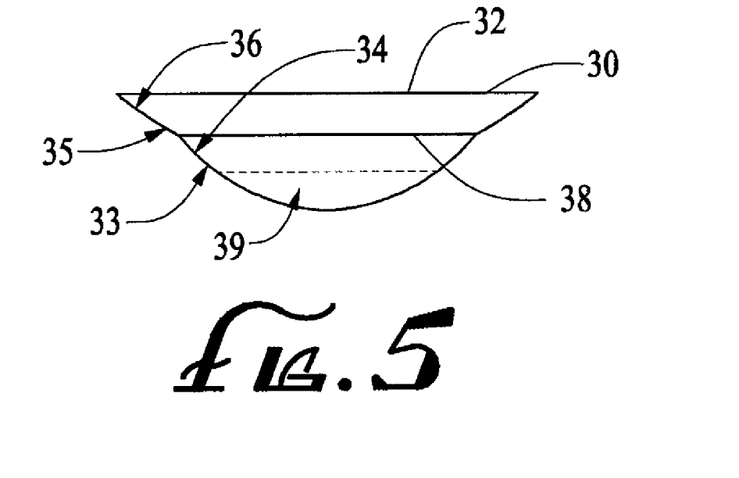
FIG. 5 is a side view of a second embodiment showing a shield incorporating features of the invention with a dual-radii base curve.
Figure 6:
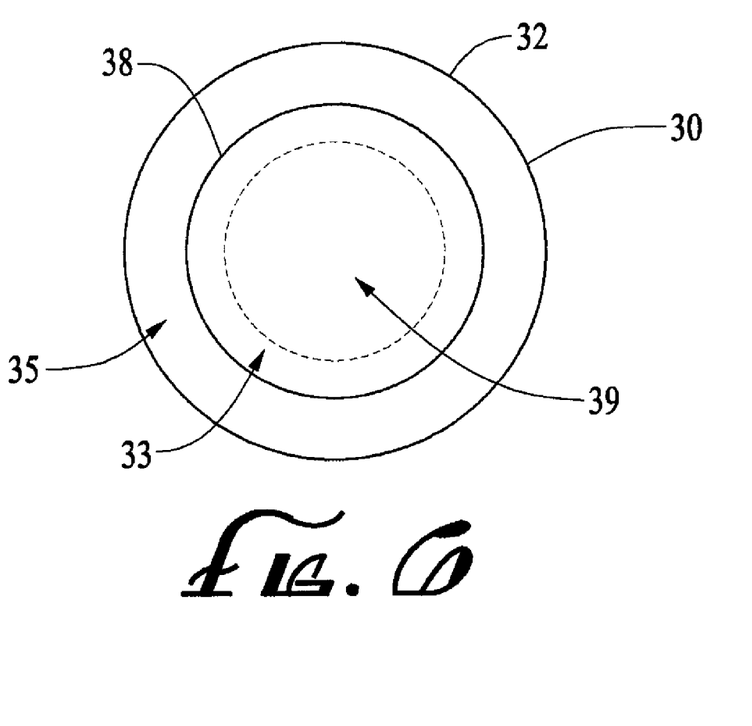
FIG. 6 is a front view of the shield of FIG. 5.

Referring to FIGS. 5 and 6, a second embodiment of the device described herein is shown. The collagen shield 30 has a dual-radii base curve with the different radii meeting in a limbal ring 38 around the shield. The scleral portion 35 of the shield has a base curve radius 36 of approximately 12.7 mm to match the radius of curvature of the scleral portion of the eye; the corneal portion 33 of the shield has a base curve radius 34 of approximately 7.7 mm to match the radius of curvature of the corneal portion of the eye. The dual base curves forming the inside curvature of the shield are designed to meet and form a limbal ring 38 around the shield. The limbal ring 38 provides an additional mechanism to keep the collagen shield centered on the eye. The diameter of the limbal ring 38 on the shield is approximately 12-13 mm which matches the limbal diameter of the cornea. The outer edge 32 of the collagen shield has a circular configuration with an outer diameter of approximately 17-18 mm. The scleral portion 35 of the base curve has a radius of curvature 36 slightly smaller than the typical radius of curvature of the scleral portion of the eye so that the outer edge 32 of the collagen shield tightly fits against the eye to prevent the edge from being rolled over by the movement of the eyelids. The central corneal portion 39 of the shield has a diameter of approximately 8-9 mm.

Figure 7:
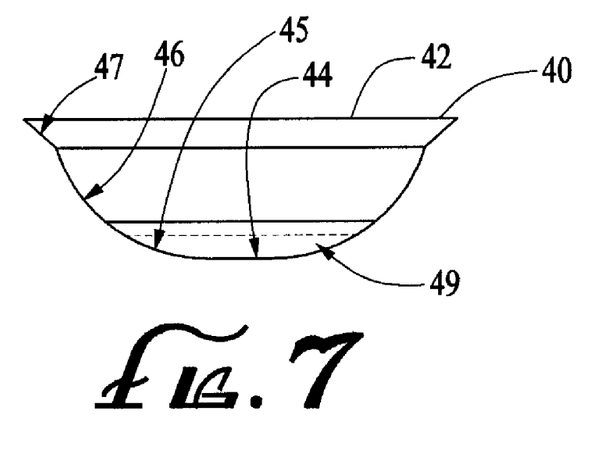
FIG. 7 is a side view of a third embodiment showing a shield incorporating features of the invention with a multi-radii base curve.
Figure 8:
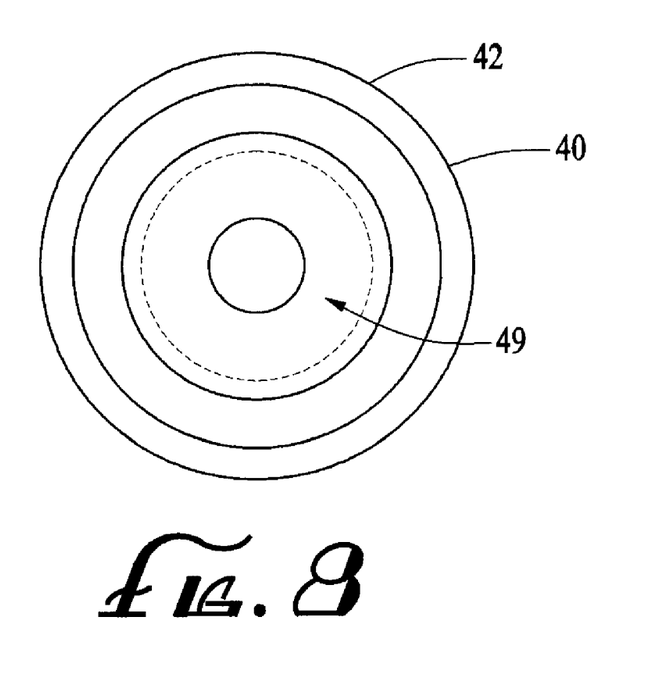
FIG. 8 is a front view of the shield of FIG. 7.

Referring to FIGS. 7 and 8, a third embodiment of the device described herein is shown. The collagen shield 40 has a multi-radii base curve typical of the base curve used for commercially available collagen corneal shields. The multi-radii base curve is made up of several radii of curvature. The central radius of curvature 44 is flat, the next radius of curvature 45 is 10.7 mm, the third radius of curvature 46 is 5 mm, and the fourth radius of curvature 47 is 12.7 mm which matches the radius of curvature of the scleral portion of the eye. When placed on the eye, this collagen shield will loosely fit over the cornea and stabilize on the scleral portion of the eye. The outer edge 42 of the collagen shield has a circular configuration with an outer diameter of approximately 17-18 mm. The scleral portion 35 of the base curve has a radius of curvature 47 slightly smaller than the typical radius of curvature of the scleral portion of the eye so that the outer edge 42 of the collagen shield tightly fit against the eye to prevent the edge from being rolled over by the movement of the eyelids. The central corneal portion 49 of the shield has a diameter of approximately 8-9 mm.

Figure 9:
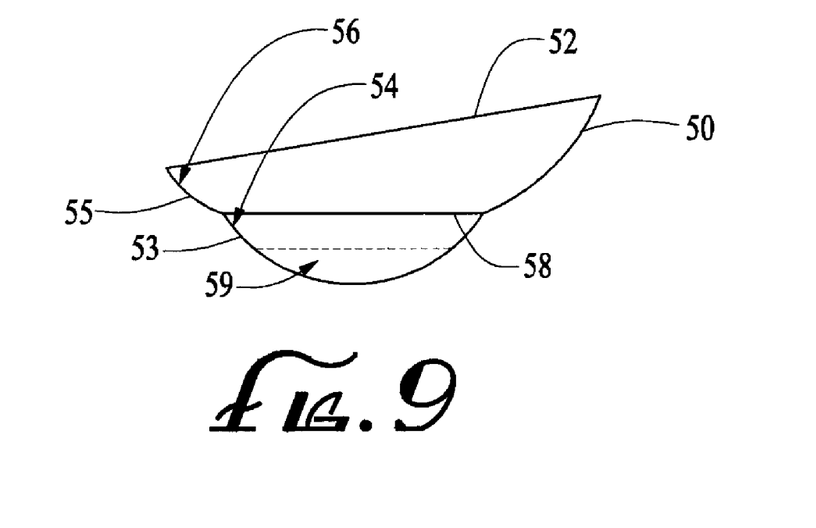
FIG. 9 is a side view of a fourth embodiment showing a shield incorporating features of the invention with a dual-radii base curve and an irregular outer edge.
Figure 10:
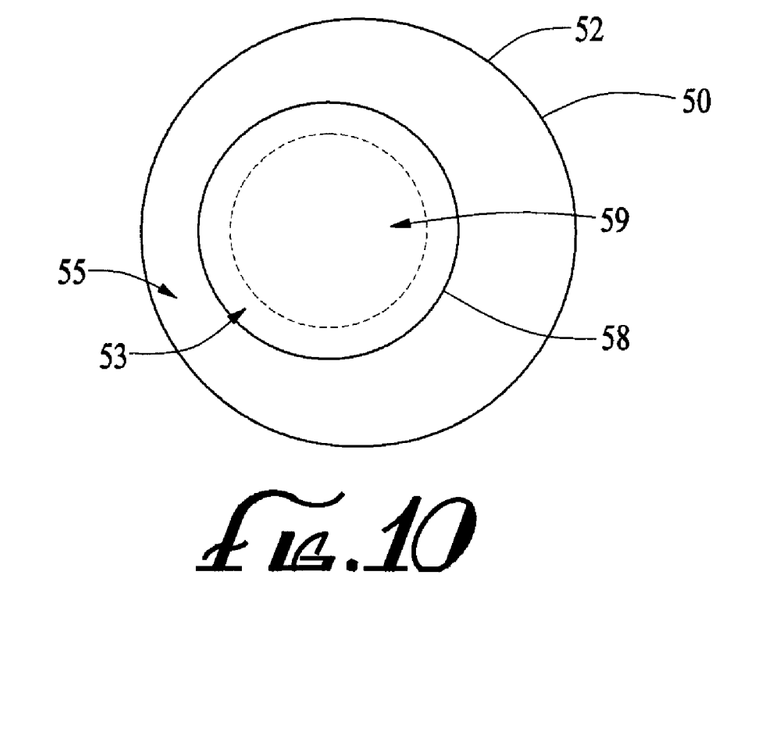
FIG. 10 is a front view of the shield of FIG. 9.

Referring to FIGS. 9 and 10, a fourth embodiment of the device described herein is shown. The collagen shield 50 has a dual-radii base curve meeting in a limbal ring 58 around the shield. The scleral portion 55 of the shield has a base curve radius 56 of approximately 12.7 mm to match the radius of curvature of the scleral portion of the eye; the corneal portion 53 of the shield has a base curve radius 54 of approximately 7.7 mm to match the radius of curvature of the corneal portion of the eye. The dual base curves forming the inside curvature of the shield are designed to meet and form a limbal ring 58 around the shield. This limbal ring provides an additional mechanism to keep the collagen shield centered on the eye. The diameter of the limbal ring on the shield is approximately 12-13 mm which matches the limbal diameter of the cornea. The outer edge 52 of the collagen shield has an irregular configuration resulting from the elongated scleral portion 55. In the fourth embodiment shown, the elongated scleral portion 55 can be formed by tilting the mold slightly during the casting operation. However, other methods can be used to form the irregular out edge including laser machining and trephining. The central corneal portion 59 of the shield has a diameter of approximately 8-9 mm.

Figure 11:
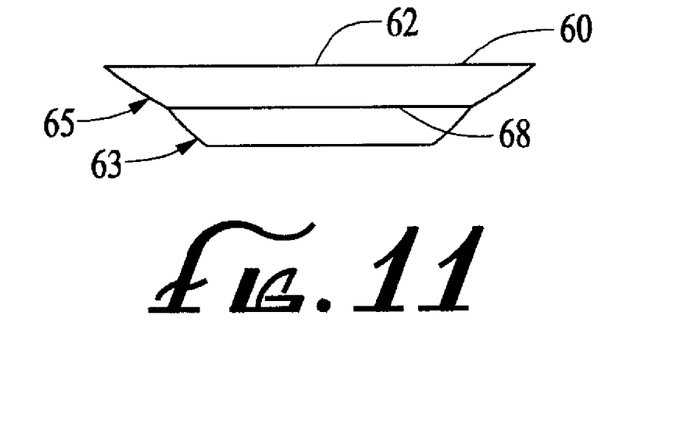
FIG. 11 is a side view of the washer remaining after the central portion of the shield of FIG. 5 has decomposed due to enzymatic degradation.
Figure 12:
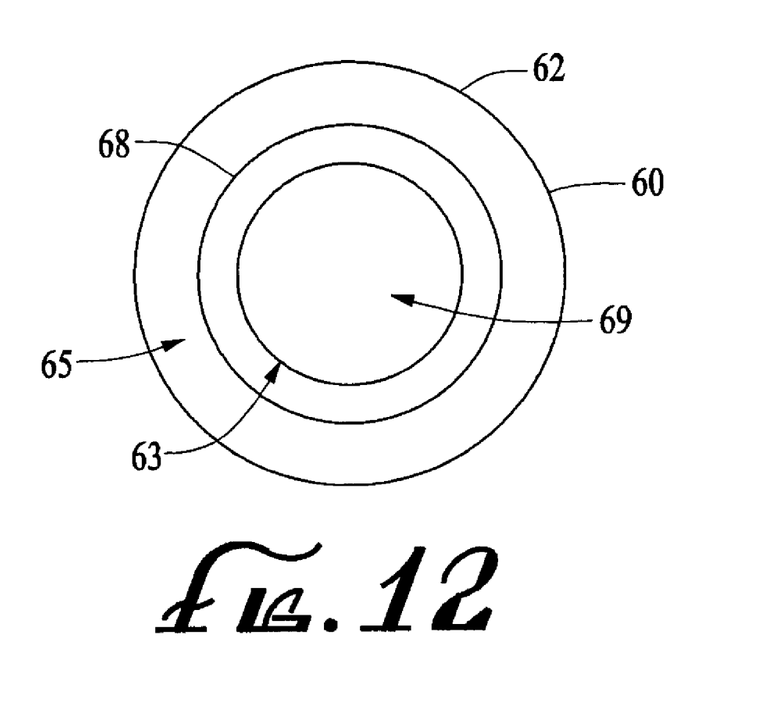
FIG. 12 is a front view of the shield of FIG. 11.

According to the invention, this central corneal portion of the collagen shield, also referred to as a first portion, is not crosslinked. The remainder of the collagen shield, referred to as a second portion, is usually crosslinked. Once the shield is applied to the eye, the central corneal portion of the shield (the first portion), which covers the optical axis of the eye, will be rapidly degraded by the enzymes contained in the tears and decompose on the eye within a short period of time, usually about a couple of hours. The decomposition time can vary as it is generally dependent on the amount of tears produced by the eye. For example, decomposition time on the eye of an individual with low tear output will generally be longer; decomposition time on the eye of an individual with high tear output can be shorter. The resultant collagen shield will now become the collagen washer 60 as shown in FIGS. 11 and 12. The scleral portion 65 and the remaining corneal portion 63 (the second portion) of the original collagen shield remain the same, only the central corneal portion 69 of the shield is no longer present. The scleral portion, the remaining corneal portion, and the limbal ring 68 serve to stabilize the collagen washer on the eye and prevent it from moving around and distorting in shape. The central collagen portion 69, which is no longer present, leaves an opening in the collagen washer having a diameter of 8-9 mm which will no longer obstruct the central corneal vision of the eye. In this way, there is no loss of vision when the collagen washer 60 opacifies on the eye.

It is anticipated that the portion of the collagen shield outside the non-crosslinked central corneal portion of the shield could consist of multiple zones having different levels of crosslinking, or no crosslinking at all. In order for there to be a non-crosslinked central corneal portion of the shield, the zone of the corneal shield adjacent to that central corneal portion must be crosslinked to some degree. Outside this adjacent zone the crosslinking may vary or be non-existent. Variations of the crosslinking may be desireable in the outer zones of the shield in order to vary the conformity of the shield to the eye over time, vary the drug dosing surface area of the shield in contact with the eye, or to alter the stability of the shield possibly to allow the shield to be pushed off the eye at a desired time interval.

The preferred material of construction of the shield is collagen having a thickness of 0.03-0.1 mm. The collagen material is crosslinked according to known techniques, preferably by exposure to UV irradiation, to provide the desired resistance to dissolution once placed on the eye. As is well known from the art, the greater the crosslinking of the collagen, the longer the collagen material will resist enzymatic degradation and remain on the eye. Without UV irradiation, a non-crosslinked collagen material will be rapidly degraded by the enzymes contained in the tears and break down or decompose on the eye within a couple of hours, usually in about 1-3.

Depending on the amount of crosslinking provided to the remaining washer portion of the collagen shield (the second portion), it will be retained on the eye from one day (24 hours) to about one week (150 hours). During this time, drugs applied to the shield or absorbed into the shield will elute from the regions of the shield in contact with the eye onto both the corneal and scleral portions of the eye. At the end of the chosen time period, the collagen washer will have either decomposed on the eye or, as it softens, be pushed off the eye by the eyelids.

Figure 13:
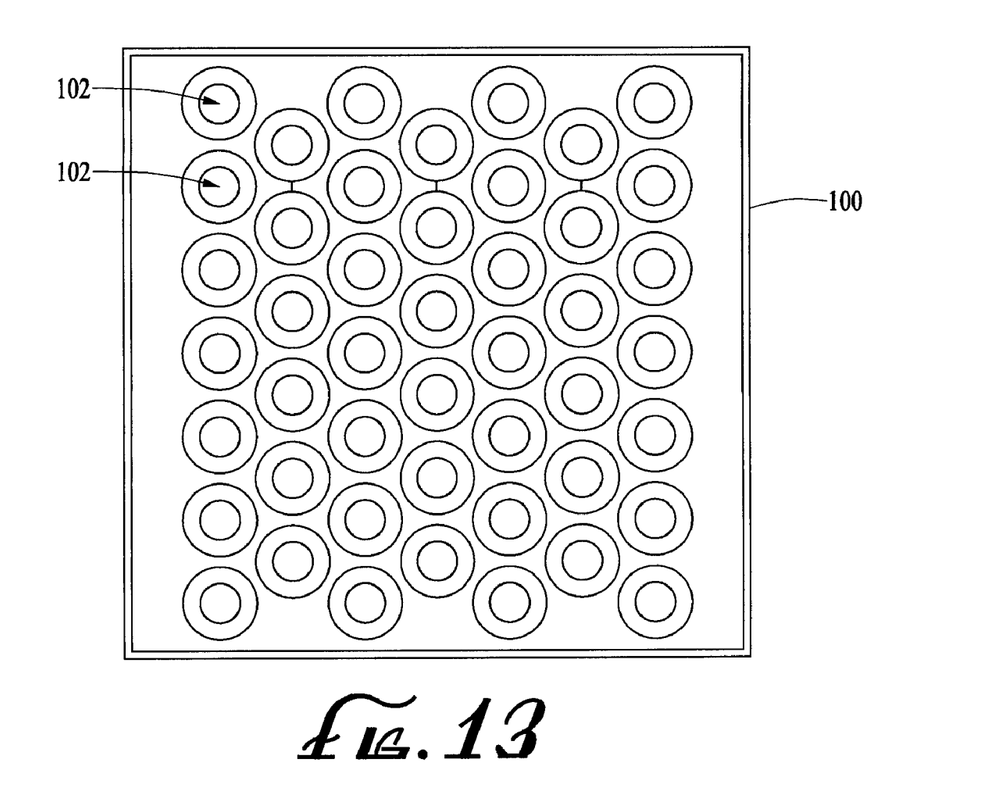
FIG. 13 is a top view of a multi-cavity mold for forming shields of FIG. 5.
Figure 14:
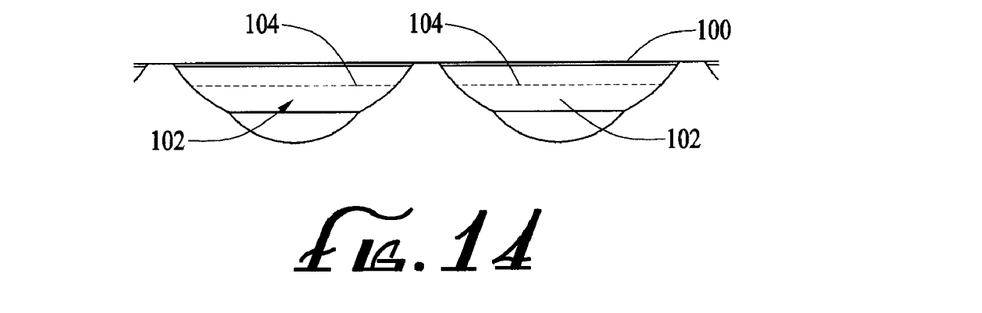
FIG. 14 is a side view showing two cavities of a multi-cavity of FIG. 13.

The same process which has been used to produce collagen corneal shields for many years is used to manufacture the collagen shield 30 shown in FIGS. 5 and 6. A multi-cavity casting mold 100 as shown in FIGS. 13-14 is used. Each cavity 102 in the mold has a shape and inner dimensions chosen to result in a dried collagen shield 30 with the desired contour and dimensions. Collagen material obtained from bovine calcaneal tendons is hydrolyzed and purified to form approximately a 3% collagen casting solution. A precise amount of the casting solution is placed into each cavity 102 of the mold and allowed to dry. As the collagen solution dries, a collagen shield is formed against the surface of the cavity in the mold. The depth of the shield 104 in the cavity, and therefore the outer diameter of the resulting collagen shield, depends upon the amount of collagen solution filled into the mold cavity.

After the shields are dry they may be removed from the mold or crosslinked while still in the mold. A patterned mask (not shown) consisting of circular spots of a UV blocking material (i.e., metal, plastic, ceramic, etc.) is placed over the dried collagen shield in order to form the non-crosslinked central corneal portion 39 of the shield as shown in FIGS. 5 and 6. The circular UV blocking spots coincide with the central corneal portion of each shield so that when the cast shields 30 are exposed to the crosslinking UV light the spots block the UV radiation from crosslinking the central corneal portion 39 of each shield. While the spot is usually round, it does not need to be. Each shield 30 with the mask over the surface is then crosslinked with UV irradiation for the time required to obtain the desired or predetermined decomposition time of the collagen when placed on the eye, preferably with sufficient resistance to decomposition to remain on the eye for at least 24 hours. The portion of the shield covered by the UV mask is not crosslinked and will be rapidly degraded by enzymes in the tears when the shield is placed on the eye thereby resulting in a contoured collagen washer with an open central corneal portion.

The outer edge of the collagen shield can be formed either by filling each cavity in the mold with a precise amount of collagen solution so that the dried collagen shield has the correct outer diameter, or the mold cavity can be overfilled with collagen, and the outer contour of the collagen shield can be cut to shape using a trephine, steel rule die, or a laser. Collagen shields with elongated scleral portions as shown in FIGS. 9 and 10 can be formed by tilting the mold several degrees and filling each cavity of the mold with a precise amount of collagen solution.

To aid in cutting the outer curvature of the shield, positioning marks can be incorporated into each cavity of the mold. Their impression in the cast collagen shield can be used during the trimming operation to position the cutting tools correctly over the collagen shield. Examples of a positioning mark would be a raised or depressed ring along the outer edge of the shield.

After the collagen shield has been formed from the collagen solution and crosslinked, it can either be provided wet by packing it in a solution such as balanced salt solution, or it can be packaged dry in the dehydrated state. The collagen shield can then be sterilized using gamma irradiation or other suitable technique.

To use the collagen shield of the present invention, such as the shield shown in FIGS. 5 and 6, the shield must be hydrated. A collagen shield packaged in a hydrating solution can be used as is. A collagen shield supplied in a dehydrated state is preferably hydrated either in a balanced salt solution or in a solution of a pharmaceutical medication to be administered to the eye prior to use. To hydrate a shield 30, it is usually placed in a balanced salt solution or a desired medication for a sufficient period of time to allow the collagen to become fully hydrated with the solution. This typically requires a few minutes, after which it will resemble a soft contact lens. The shield is then placed on the eye by medical personnel in a manner similar to the placement of a contact lens onto the eye. The central (previously masked first portion) corneal portion of the shield immediately begins to enzymatically degrade on the eye, the decomposition taking generally about a couple hours to complete. The remainder of the shield (the crosslinked second portion) now has a washer shape and will remain on the eye for a desired time which is dependent on the amount of UV crosslinking applied to the shield. Eventually, the collagen washer will decompose on the eye or, once softened by enzymatic degradation, be pushed off the eye by the eye lids.

The rate of enzymatic degradation depends on several factors. The primary factor is the amount of UV irradiation induced crosslinking in the collagen. The secondary factor is the amount of enzymes present on the eye. A patient having a dry eye will not have much tear volume and therefore will have a low volume of enzyme present. Collagen will take longer to decompose on this type of eye. A patient with a wetter eye, or a diseased eye, will have a greater amount of tear volume and therefore more enzyme. Collagen will decompose on this type of eye much faster.

Advantages of the shield of this invention over an initially washer-shaped shield include the ease of handling and placement of the shield of this invention. The shield supplied as a washer or ring easily folds over and changes shape as it is being placed onto the eye. It can be easily stretched and distorted and will not necessarily return to its original shape. On the other hand, the shield with the intact, non-crosslinked central corneal portion is much easier to handle and can be applied in the same manner as a contact lens because it retains its shape when placed over the eye. It does not stretch and distort when being applied to the eye, and tends to retain its original shape on the eye after the central corneal portion has decomposed.

While preferred embodiments with non-crosslinked and crosslinked regions, and preferred dimensions to affix the shield to the eye are described above, one skilled in the art will recognize that the shield can be prepared with other regions of non-crosslinking or crosslinking and other radii of curvature and diameters to match particular patient's who may have abnormal eye structure or dimensions. Also, while the preferred material of construction is collagen other material formed into the shape and having the crosslinking and dimensions set forth herein which can be degraded by the enzymes contained in the tears can also be used. As a further alternative, materials that dissolve in the tears rather then decompose could also be used. Alternative materials include, but are not limited to, hyaluronic acid or compositions of collagen with other materials.

I claim:

1. A device for placement on the outer surface of the eye to provide protection of the eye, delivery of drugs to the eye, or provide both protection and drug delivery to the eye, without obstructing vision, comprising
   a) a contoured collagen shield with one or more base curve radii selected to provide retention of the shield on the eye, a first portion of the shield configured to cover a central portion of the cornea and a second portion of the shield extending outward from the first portion and forming a ring around the first portion,
   b) the first portion of the shield comprising non-crosslinked collagen configured for rapid decomposition in the presence of enzymes in the tears, and
   c) the second portion comprising crosslinked collagen having a decomposition rate in the presence of enzymes in the tears over a period of time slower than the first portion.

2. The device of claim 1 wherein the first portion of the shield once placed on the eye is substantially decomposed within about 1 to about 3 hours providing an opening in the shield over the central portion of the cornea.

3. The device of claim 1 wherein the cross linking of the second portions of the shield provides a predetermined resistance to enzymatic degradation once placed on the eye.

4. The device of claim 3 wherein the second portion of the shield has sufficient resistance to enzymatic degradation to remain on the eye from 24 hours to about 150 hours.

5. The device of claim 1 wherein the corneal shield has a dual radii base curve such that a portion of the shield covering the cornea has a base curve radius substantially equivalent to the radius of curvature of the cornea, and a second portion of the shield covering the sclera has a base curve radius substantially equivalent to the radius of curvature of the sclera.

* * * * *